United States Patent [19]

Schlicht

[11] Patent Number: 4,559,152

[45] Date of Patent: Dec. 17, 1985

[54] FRICTION-REDUCING MOLYBDENUM SALTS AND PROCESS FOR MAKING SAME

[75] Inventor: Raymond C. Schlicht, Fishkill, N.Y.

[73] Assignee: Texaco Inc., White Plains, N.Y.

[21] Appl. No.: 389,339

[22] Filed: Jun. 17, 1982

Related U.S. Application Data

[63] Continuation-in-part of Ser. No. 188,488, Sep. 18, 1980, abandoned.

[51] Int. Cl.$^4$ .................. C16M 1/48; C16M 5/24
[52] U.S. Cl. .................. 252/32.7 E; 252/327 HC; 556/25
[58] Field of Search .................. 252/32.7 HC, 32.7 E; 260/429 K

[56] References Cited

U.S. PATENT DOCUMENTS

| | | | |
|---|---|---|---|
| 2,368,000 | 1/1945 | Cook et al. | 252/32.7 E X |
| 2,806,022 | 9/1957 | Sabol | 252/32.7 HC X |
| 2,962,493 | 11/1960 | Sabol et al. | 252/32.7 HC X |
| 3,400,140 | 9/1968 | Rowan et al. | 252/32.7 E X |
| 3,402,188 | 9/1968 | Wiese | 252/32.7 E X |
| 3,494,866 | 2/1970 | Rowan et al. | 252/32.7 R |
| 3,840,463 | 10/1974 | Froeschmann et al. | 252/32.7 E X |
| 4,202,781 | 5/1980 | Sabol et al. | 252/32.7 HC |
| 4,208,292 | 7/1980 | Bridger | 252/32.7 E |

OTHER PUBLICATIONS

Hawley, G. G. (Editor), "The Condensed Chemical Dictionary", 9th Edition, p. 588, 1977.

*Primary Examiner*—William R. Dixon, Jr.
*Assistant Examiner*—Cynthia A. Prezlock
*Attorney, Agent, or Firm*—Robert A. Kulason; James J. O'Loughlin

[57] ABSTRACT

Molybdenum salts of organophosphorus acids prepared in the presence of polar solvents are found to have a higher conversion of molybdenum than if otherwise produced. The salts of the invention are useful as lubricating oil additives to reduce friction and corrosion and to decrease fuel consumption in internal combustion engines.

12 Claims, No Drawings

FRICTION-REDUCING MOLYBDENUM SALTS AND PROCESS FOR MAKING SAME

CROSS-REFERENCE TO CO-PENDING APPLICATION

This application is a continuation-in-part of coas-signed application Ser. No. 188,488, filed Sept. 18, 1980 and now abandoned.

BACKGROUND OF THE INVENTION

1. Field Of The Invention

This invention is concerned in one aspect, with the preparation of novel molybdenum salts of dialkyldithiophosphoric acids and other organo-phosphorus acids by reaction of an aqueous molybdic acid solution with the desired phosphorus acid in the presence of an inert solvent mixed with a polar solvent, preferably ethyl acetate or other esters, and with their use as lubricating oil additives. In another aspect, the invention relates to reducing fuel consumption by adding these additives to the lubricants used.

2. Description of Prior Disclosures

There are numerous patents and literature references on molybdenum salts of dialkyldithiophosphoric acids and related acids. This background disclosure therefor is restricted to those which are believed most relevant.

Two patents, U.S. Pat. Nos. 3,400,140 and 3,494,866, disclose compounds $[(RO)_2PSS]_2Mo_2S_2O_3$ prepared by reaction of two moles of the phosphorus acid with one mole of molybdic acid (acidified aqueous $Na_2Mo_4$ or ammonium molybdates) in the presence of a hydrocarbon as the only organic solvent. In the patented art, the products retain only one-half of the dialkyldithiophosphoric acid charged (i.e. the claimed composition has a Mo:P atomic ratio=1:1). Also, the products are claimed to possess a S:P ratio greater than the 2:1 in the charge; hence the increased S:P ratio must arise by transfer of the additional sulfur from the half of the acid which is not otherwise used in the reaction.

Patents cited in the above-mentioned patent application include U.S. Pat. Nos. 3,402,188; 4,202,781; 2,368,000; 2,806,022 and 2,962,493. Of these, the first discloses molybdenum salts of organophosphorus acids having the structural formula:

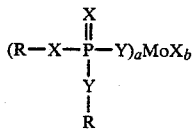

wherein R is hydrocarbyl; X is sulfur or oxygen; a and b are integers with (a+2b) being 4 to 8. The patentee discloses various methods for preparing these salts including one involving the reaction of an organophosphorus acid with molybdenum trioxide or dioxide which is promoted by the addition of water or a lower alcohol. Indifferently, the reaction may be carried out by mixing the molybdenum compound with the acid in water and then adding water; they may be initially reacted in benzene followed by the addition of methanol; or the aqueous mixture after reaction is treated with naphtha and benzene.

U.S. Pat. No. 4,202,781 shows the preparation of molybdenum-phospho-sulfurized hydrocarbons by reacting the hydrocarbon optionally in a diluent inert hydrocarbon with an aqueous solution of a molybdenum compound and removing the molybdenum-depleted aqueous phase by distillation or partitioning. The patentee indicates that oxygen-containing solvents are limited as diluents for they cause emulsions owing to their poor solubility in the aqueous phase.

U.S. Pat. No. 2,368,000 describes the preparation of barium, calcium, zinc, aluminum and tin salts of dithiophosphoric acid esters by dissolving a diester in a low boiling mixture containing unstated proportions of non-polar and polar solvents, such as an alcohol and a hydrocarbon and adding to the resulting mixture a metal oxide. Similarly, U.S. Pat. No. 2,806,022 describes the preparation of neutralized reaction products of a phosphorus sulfide and a hydrocarbon with an alkali metal or alkaline earth metal compound wherein the neutralization is carried out in the presence of between 0.5 and 2 moles of water per mole of compound and 2 to 20 moles of an alkanol per mole of metal compound and heating to remove the water and alkanol. U.S. Pat. No. 2,962,493 improves on the previous patent by refluxing a hydrolyzed hydrocarbon-phosphorus sulfide with the above solvents prior to neutralization with the metal compound.

In contradistinction to the alkali and alkaline earth metal oxides employed in the above-discussed three patents, molybdenum oxides such as $MoO_3$ react with acids only under the special conditions provided by very strong mineral acids and reducing acids. Molybdenum oxides are in fact acid anhydrides and react substantially with bases. Thus the chemistry of molybdenum oxides differs drastically from that of the heavy metal oxides such as $Fe_2O_3$, PbO, ZnO, CaO, and BaO. This is known, for example from page 779 of "Advanced Inorganic Chemistry" by F. Albert Colton and B. Wilkenson, Interscience Publishers, John Wiley and Sons, 1962. Discussing the second transition series of elements, the authors state: "The most important of the oxides are $MoO_3$ and $WO_3$ . . . They are not attacked by acids but dissolve in bases to form molybdate and tungstate solutions . . . It ($MoO_3$) is the anhydride of molybdic acid but it does not form hydrates directly."

The present invention is predicated on the unobvious discovery that molybdenum salts of certain organo-phosphorus acids, when prepared in a mixture of solvents and polar cosolvents present in a certain proportion have a higher conversion of molybdenum and phosphorus than is produced in the absence of such a mixture. The polar organic solvent functions to solubilize the molybdic acid (or other hydrous molybdenum oxides) into the organic phase. As a consequence, the subject products are compositionally different from those of the prior art in that the resulting molybdenum salts have Mo:P ratios which approach the ratio of the charge.

In the practice of the invention, an essentially 1:1 Mo:P ratio in the product may be attained without need to employ a sacrificial amount of excess phosphorus acid. Another difference from the prior art is that water is removed by azeotropic distillation before recovering the product by filtration and stripping. These differences from the prior art result in a more convenient, lower cost process which minimizes the need to dispose of unreacted Mo and P into the environment.

As will be seen hereinafter, none of the prior art references known to the applicant discloses, hints or suggests in any manner whatsoever applicant's novel, unique and unobvious process and products.

SUMMARY OF THE INVENTION

The present invention provides novel oil soluble salts of organophosphorus acids which are prepared by a process involving reacting an aqueous solution of an oxymolybdenum compound with a solution of at least one organophosphorus acid in an inert solvent mixed with a polar cosolvent. The reaction is readily conducted at room temperature to 80° C. and preferably at about 30° to about 80° C. The water formed in the reaction is removed by azeotropic distillation and the product is recovered by filtration and stripping of the solvent and cosolvent. The present invention also provides lubricants containing the salts and a method for reducing fuel consumption in an internal combustion engine by treating the moving surfaces thereof with these lubricants.

The salts of the invention have the following formulas:

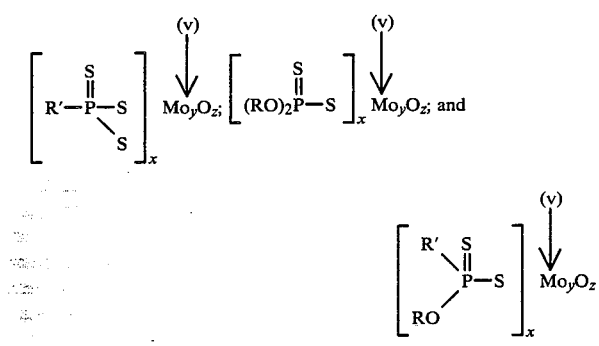

where $X = 1$ to $5y$, $y = 1-8$, $v =$ the valence state of molybdenum, $$z = \frac{(v \cdot y) - x}{2},$$

v ranges from 3 to 6: and R' is an alkenyl group having 4 to 200 carbon atoms.

The preferred organophosphorus acids are the dialkyldithiophosphoric acids, olefin:$P_2S_5$ reaction products and alcoholyzed olefin:$P_2S_5$ products. There are 3 to 30 carbon atoms in the chain of either the alkyl or the olefin moieties, (R). An example of a suitable R group is n-tetradecenylsuccinimidylethyl. The substituent R may be unsubstituted or one or more of its substitutable hydrogens may be replaced by a non-interfering substituent such as alkyl, haloalkyl, nitro, cyano, halo.

Any oxy compound of molybdenum wherein the molybdenum is present in the tri-to hexavalent state may be employed as the molybdenum source in the practice of this invention. Such compounds include molybdenum trioxide, molybdic acid, ammonium molybdate, sodium molybdate, potassium molybdate, other alkali metal molybdates, and other molybdenum salts such as $MoOCl_4$, $MoO_2Br_2$, $Mo_2O_3Cl_6$, and $MoOF_4$. Molybdenum trioxide may also be employed by dissolving it in aqueous ammonia or alkali base followed by treatment with a mineral acid which in essence, converts the oxide to molybdic acid (or its polymolybdic acid form).

The process of this invention is conducted in an inert solvent which may be hexane or other hydrocarbons including the oil to which the additive is to be added.

The preferred polar organic cosolvents employed are ethyl acetate, ethylene glycol dimethyl ether, and isopropanol. However, other esters, ethers, and alcohols as well as ketones, lactones, amides, lactams and other polar cosolvents and mixtures thereof also can be used with various degrees of effectiveness. The ratios of polar solvent to hydrocarbon may vary from about 1:10 to 10:1 with the optimum in solvent ratio range varying with choice of solvents. Also, the alcohols used in excess to prepare the dialkyldithiophosphoric acid may also function as the polar solvent.

DESCRIPTION OF THE BEST MODE OF THE INVENTION

The invention is illustrated in non-limiting fashion by the following examples. In these examples, Example Ia and Ib compare the preparation of a molybdenum dialkyldithiophosphate by the two methods, using mole ratios of dialkyldithiophosphoric acid and "$H_2MoO_4$" substantially greater than 1:1 to approximate the ratios used in the prior art. The first example (a) illustrates a preparation according to the invention using a polar organic solvent in addition to the hydrocarbon solvent and water, while the second example (b) used the single organic solvent system of the prior art. Examples IIa, IIb and IIc make a similar comparison using a 1:1 mole ratio of the dithiophosphoric acid: "$H_2MoO_4$". In all of these examples, a solution of a dialkyldithiophosphoric acid in a hydrocarbon solvent was prepared from a mixed normal $C_{12}/C_{14}$ alcohol ("Epal 1214" from Ethyl Corporation) by reaction of the alcohol with $P_2S_5$, using a 4.2:1 mole ratio, respectively, at 70°-80° C. over 4 hours. The solution was filtered and titrated with standard 0.1N KOH solution to determine its active concentration.

EXAMPLE Ia

This example illustrates the preparation of a molybdenum di-n-$C_{12-14}$ alkyldithiophosphate using ethyl acetate co-solvent; P:Mo charge ratio=1.66:1, according to the invention.

A solution of 29.0 g. (0.12 mole) of $Na_2MoO_4.2H_2O$ in 30 ml. water was treated with 12.0 g. (0.12 mole) conc. $H_2SO_4$ at 30°-60°. Then 169.2 g. of a n-heptane solution of 0.2 mole of the di-n-$C_{12-14}$ alkyldithiophosphoric acid was added at 30°-40° which was followed by the addition of 200 ml. ethyl acetate and 30 ml. n-heptane. The mixture changed color evidencing an oxidation reduction and was total-refluxed at 72° C. for ½ hour, and then the water was removed by azeotropic distillation over 3 hours at 78° C., maximum. The mixture was then filtered at room temperature and stripped to 80° C. at 10 mm. The yield was 124 g. of blue product. The elemental analysis are given in Table I.

EXAMPLE Ib

This example shows the preparation of a molybdenum (di-n-$C_{12-14}$alkyldithiophosphate without a polar organic cosolvent; charge ratio of P:Mo=1.5:1.

A solution of 20.75 g. (about 0.08 mole) of $Na_2Mo_4.2H_2O$ in 25 ml. water was treated with 7.80 g. (0.078 mole) concentrated $H_2SO_4$ at 30°-60°. Then 201.5 g. of a solution of 0.13 mole of the di-n-$C_{12-14}$ alkyldithiophosphoric acid in cyclohexane was added at 30°-40° C. along with 240 ml. more cyclohexane. Cyclohexane was selected to give the same reflux temperature as the heptane/ethyl acetate mixture used in the previous example. The mixture was total refluxed for ½ hour at 73°

C., and then the water was removed by azeotropic distillation over 3 hours at 81° C., maximum. The mixture was cooled, filtered, and then stripped to 80° C. at about 10 mm pressure. The yield was 74.5 g. of a clear, blue product. The elemental analyses are given in Table I.

EXAMPLE IIa

This example shows the preparation of a molybdenum di-n-$C_{12-14}$ alkyldithiophosphate with ethyl acetate as cosolvent; charge ratio of P:Mo=1:1, according to the invention.

A solution of 116 g. (0.48 mole) $Na_2MoO_4.2H_2O$ in 120 ml. water was treated with 48.0 g. (0.48 mole) conc. $H_2SO_4$. Then 100 ml. n-heptane, 400 ml. ethyl acetate, and 406.1 g. of a heptane solution of 0.48 mole of di-n-$C_{12-14}$ alkyldithiophosphoric acid were added. The reaction was carried out as in Example Ia, resulting in 334 g. of a deep blue product. The analyses are given in Table I.

EXAMPLE IIb

This example shows the preparation of a molybdenum di-n-$C_{12-14}$ alkyldithiophosphate without the use of a polar cosolvent; charge ratio of P:Mo=1:1.

A slurry of 48.4 g. (0.20 mole) of $Na_2Mo_4.2H_2O$ in 120 ml n-heptane was treated at 30°–60° C. with a solution of 20.0 g. (0.20 mole) concentrated $H_2SO_4$ in 40 ml. water. Transfer of the $H_2SO_4$ solution was completed, using an additional 10 ml. water.

The mixture was cooled in room temperature, and then 178.0 g of a solution of 0.20 mole of the di-n-$C_{12-14}$ alkyldithiophosphoric acid in an approximately 1:1 (vol) misture of n-heptane and toluene was added to room temperature. The mixture was then heated to 70° C. under $N_2$ where it was stirred for 0.5 hours under total reflux conditions. Finally the mixture was heated to active reflux, removing water by azeotropic distillation over 3 hours at 86°–105° C. The essentially water-free mixture was filtered at room temperature, and the filtrate was stripped to 80° at about 10 mm pressure. The yield was 109 g. The elemental analyses are given in Table I.

EXAMPLE IIc

This example shows the preparation of a molybdenum di-n-$C_{12-14}$ alkyldithiophosphate with ethylene glycol dimethyl ether as organic cosolvent; charge ratio of P:Mo=1:1, according to the invention.

A solution of 58.00 g. (0.24 mole) $Na_2MoO_4.2H_2O$ in 60 ml. water was treated with 24.0 g. (0.24 mole) concentrated $H_2SO_4$ as in Example Ia. Then 201.0 g. of a heptane solution of 0.24 mole of the di-n-$C_{12-14}$ alkyldithiophosphoric acid was added along with 50 ml. n-heptane and 200 ml. of ethylene glycol dimethyl ether. The reaction was carried out as in Example Ia, and the reaction mixture was worked up to give 38 g. product. See Table I for the analyses.

EXAMPLE IId

This example shows the preparation of a molybdenum di-n-$C_{12-14}$ alkyldithiophosphate with isopropyl alcohol as the organic cosolvent; charge ratio of P:Mo:1:1, according to the invention.

The same materials as in Example IIc were used except (1) 100 ml. isopropyl alcohol was substituted for the ethylene glycol dimethyl ether and (2) the additional hydrocarbon solvents were 50 ml. n-heptane and 100 ml. cyclohexane, the latter to depress the reflux temperature to about the same initial temperature as in Example IIb. The yield was 143 g. of product. Table I gives the analyses.

The analytical results in Table I demonstrate that, in the absence of a polar cosolvent, the conversion of the molybdenum to product is substantially incomplete. Unexpectedly, when a polar cosolvent (ethyl acetate) is used, the conversion to product is essentially complete (greater than 90%). Similarly, when ethylene glycol dimethyl ether and isopropanol were used as cosolvents, the conversion of molybdenum was much improved over the example with no polar solvent.

The following examples in Table II illustrate the extension of the subject invention to the preparation of molybdenum salts of other dialkyldithiophosphoric acids. The procedures were essentially identical to the examples previously described. The degree of conversion to molybdenum salts was found to range from 65 to 100%.

TABLE I

COMPARISON OF ANALYSES OF Mo Di-$N_{12-14}$ ALKYLDITHIOPHOSPHATES PREPARED WITH POLAR COSOLVENT VS. HYDROCARBON ONLY AS REACTION SOLVENTS

| Example No. | Solvents Used Hydrocarbon | Co-Solvent | Charge Ratio of Mo:P | Calc'd. % Mo | % P | Product Analysis % Mo | % P | Mo:P At. Ratio | (% of Theory) |
|---|---|---|---|---|---|---|---|---|---|
| Ia | n-Heptane | Ethyl acetate | 0.6:1 | 9.8 | 5.3 | 8.7 | 5.0 | 0.56:1 | (93.3) |
| Ib | Cyclohexane | None | 0.65:1 | 10.5 | 5.2 | 3.6 | 5.2 | 0.22:1 | (33.8) |
| IIa | Heptane | Ethyl acetate | 1:1 | 14.9 | 4.8 | 13.3 | 4.6 | 0.93:1 | (93) |
| IIb | Heptane/ toluene | None | 1:1 | 14.9 | 4.8 | 5.8 | 5.3 | 0.35:1 | (35) |
| IIc | Heptane | Ethylene glycol di-methyl ether | 1:1 | 14.9 | 4.8 | 7.12 | 4.6 | 0.50:1 | (50) |
| IId | Heptane/ cyclohexane | i-Propyl Alcohol | 1:1 | 14.9 | 4.8 | 8.73 | 5.0 | 0.57:1 | (57) |

TABLE II

PREPARATION OF OTHER MOLYBDENUM DIALKYLDITHIOPHOSPHATES USING A HYDROCARBON:ETHYL ACETATE SOLVENT SYSTEM

| Example No. | Alkyl Group In Dithiophosphate | Hydrocarbon Solvent | Charge Ratio Mo:P | Calculated % Mo | % P | Product Analyses % Mo | % P | Mo:P At. Ratio | (% of Theory) |
|---|---|---|---|---|---|---|---|---|---|
| III | 2-Ethylhexyl | n-Heptane | 0.6:1 | 13.4 | 7.2 | 8.89 | 7.36 | 0.39:1 | (65) |
| IV | 2-Ethylhexyl | n-Heptane | 1:1 | 19.6 | 6.33 | 14.81 | 6.51 | 0.73:1 | (73) |
| V | Isopropyl | n-Heptane | 0.5:1 | 17.3 | 11.2 | 17.39 | 10.1 | 0.56:1 | (111) |

TABLE II-continued

PREPARATION OF OTHER MOLYBDENUM DIALKYLDITHIOPHOSPHATES
USING A HYDROCARBON:ETHYL ACETATE SOLVENT SYSTEM

| Example No. | Alkyl Group In Dithiophosphate | Hydrocarbon Solvent | Charge Ratio Mo:P | Calculated % Mo | % P | Product Analyses % Mo | % P | Mo:P At. Ratio | (% of Theory) |
|---|---|---|---|---|---|---|---|---|---|
| VI | Isopropyl | n-Heptane | 0.25:1 | 9.96 | 12.9 | 7.90 | 14.5 | 0.18:1 | (70) |
| VII | 2-(n-Tetradecenyl succinimidyl) ethyl | n-Heptane | 1:1 | 5.12 | 1.65 | 4.89 | 1.5 | 1.05:1 | (105) |

The analyses and calculated values of Table III demonstrate that products may be prepared by the process of this invention which are compositionally different from the prior art patents, particularly with regard of retention of about 96% of the phosphorus charged versus only 50% in the prior art. This is particularly important in applications of the additives in lubricants, where the phosphorus content in a large measure determines the oxidation, corrosion, and wear preventative properties of the additive.

When ethyl acetate is used as solvent, the products after stripping to a high temperature at less than 1 mm. vacuum, still retain some ester, as evidenced by a strong carbonyl bands at 1740 cm$^{-1}$ in their IR spectra; this indicates that complexation of the ester with the molybdenum moiety occurs.

Another difference between the subject products (Example III and Example IV) and a commercial molybdenum di-2-ethylhexyldithiophosphate (Molyvan L from R. T. Vanderbilt Co.) is the color and storage stability of the additive blended into oil formulations. At identical concentrations of Mo (0.08% Mo), oils containing the subject products are blue and remain sediment-free for weeks, while the commercial additive gives a green oil blend which deposits a sediment in a few hours.

TABLE III

COMPARISON OF PRODUCTS OF SUBJECT INVENTION
TO PRODUCTS OF U.S. PAT. NO. 3,400,140

| | PRODUCTS OF SUBJECT INVENTION | | | | | RELATED PRIOR ART PRODUCTS (1) | | |
|---|---|---|---|---|---|---|---|---|
| Example No. | R Group | % S | % P | % Mo | At Ratio S:P:Mo | % S | S:P:Mo | Example No.[b] |
| V | i-Propyl | 20.5 | 10.1 | 17.39 | 3.5:1.8:1 | 25.52 | 3:1:1[a] | I |
| III | 2-Ethylhexyl | 12.8 | 7.2 | 13.4 | 2.9:1.7:1 | — | 3:1:1[a] | II |
| Ia | n-C$_{12-14}$ alkyl | 7.7 | 5.0 | 8.7 | 2.7:1.8:1 | Not available | | |

[a]The claimed atomic ratio; there were no molybdenum or phosphorus analyses given in Example I, nor a sulfur analysis for Example III.
[b]The prior art example numbers are the same in both patents.
(1) Comparisons are made for reactions using the same dialkyldithiophosphoric acid and in about the same mole ratio of about 1 mole molybdenum reactant: 2 of the acid.

The following examples illustrate the use of the subject process to prepare molybdenum salts of organophosphorus acids derived from an intermediate olefin: P$_2$S$_5$ reaction product.

EXAMPLE VIII

Preparation of a 2:1 (molar) n-Octadecene-1: P$_2$S$_5$ Reaction Product

A mixture of 504.0 g. (2.0 moles) n-octadecene-1 and 222 g. (1.0 mole) P$_2$S$_5$ were heated under N$_2$ to 140° where an exotherm raised the temperature to 155°. After heating to 190°, the mixture was cooled, dissolved in cyclohexane, and filtered. Stripping under vacuum to 100° at 10 mm. gave 695 g. of product. The analyses were 9.1% P and 18.5% S (vs. 8.95% and 18.5%, respectively calculated for the structure (C$_{18}$H$_{35}$)$_2$P$_2$S$_4$).

EXAMPLE IX

Preparation of a 2:1 (Molar) n-Tetradecene-1:P$_2$S$_5$ Reaction Product

Same as Example VII, except the olefin used was 431:2 g (2.0 mole) tetradecene-1, and the reaction was conducted at 180° for 5 hours. The reaction mixture was filtered in n-heptane solution, and stripped to 150° at 10 mm. The product yield was 6.21 g., and the analytical results were 10.0% P and 20.5% S (vs. 10.0% and 20.7% calculated for (C$_{14}$H$_{27}$)$_2$P$_2$S$_4$).

The intermediate products of Example VII and IX (R''$_2$P$_2$S$_3$) have the structure:

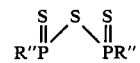

where R'' is an alkenyl group derived from a linear or branched olefin having from 4 to 40 carbons and preferably 8 to 20, such as n-tetradecenyl and n-octadecenyl. However, cyclic or linear polymers of the structure:

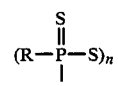

may also be present as well as various side-reaction products.

The following examples illustrate some alcoholysis products of a thioanhydride, which has the structure:

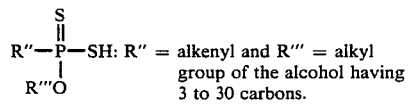

R'' = alkenyl and R''' = alkyl group of the alcohol having 3 to 30 carbons.

preferably, R" is n-tetradecenyl or n-octadecenyl and R'" is derived from a mixture of n-dodecyl and n-tetradecyl alcohols.

EXAMPLE X n-Tetradecene-$P_2S_5$ Product Alcoholyzed with a n-$C_{12-14}$ alcohol mixture A 116.0 g (0.4 g. at phosphorus) quantity of the n-tetradecene-$P_2S_5$ product of Example IX was mixed with 79.2 g. (0.4 mole) of a n-$C_{12-14}$ alcohol mixture (Epol 1214 from the Ethyl Corp.), and heated under $N_2$ at 80° C. for 2 hours. The yield was essentially quantitative. The analyses were as follows:

|  | Found | Calculated |
|---|---|---|
| % P | 5.9 | 6.35 |
| % S | 11.7 | 13.1 (per two S) |
| Saponification No. | 104 | 115 (per one acid H) |
| Mol. wt. | 435 | 448 |

EXAMPLE XI n-Tetradecene: $P_2S_5$ Product Alcoholyzed with Isopropyl Alcohol

A 309.6 g. (1.0 g. at. phosphorus) quantity of a n-tetradecene: $P_2S_5$ product prepared as in Example IX (having 9.5% P and 19.4% S) was treated with 90.0 g. (1.5 mole) of isopropanol at 80° C. for 3 hours and 90° C. for 4 hours. The reaction mixture was stripped at 80° and 10 mm. to remove unreacted alcohol, yielding 332 g. of product. The analyses were as follows: % P=8.3, % S=17.8 vs. 8.4 and 17.3, respectively, calculated. The preparations of molybdenum derivatives of the olefin: $P_2S_5$ products of Examples VIII–XI are described next.

EXAMPLE XII

Preparation of a Molybdenum Derivative of a n-Octadecene-1:$P_2S_5$ Product: Hydrocarbon Solvents To a solution at room temperature of 36.3 g. (0.15 mole) sodium molybdate 0.2$H_2O$ in 50 ml. water, 15.0 g. (0.15 mole) conc. $H_2SO_4$ was added at 60° max. Then 103.8 g. (0.3 g. at P) of a 2:1 mole ratio n-octadecene: $P_2S_5$ product (Example VIII) dissolved in 150 ml. n-heptane was added, followed by 120 ml. toluene. After 1 hour total reflux at 82° C., water (55 ml.) was removed by azeotropic distillation over 5 hours at 103° C., max. The mixture was cooled to room temperature, filtered, and stripped to 100° C. at 10 mm. The yield was 112 g of a deep blue product. See Table IV for the elemental analyses.

EXAMPLE XIII

Preparation of Molybdenum Derivative of a n-Octadecene-1:$P_2S_5$ Product: Ethyl Acetate as Primary Solvent The same materials as in Example XII were used, except 200 ml. ethyl acetate was used in place of the toluene and only 50 ml. n-heptane was charged to enhance water separation in the aceotropic distillation step. After 6 hours at 87° C. maximum, 55 ml. aqueous distillate was removed. On work-up, 123.4 g. semi-solid product was obtained. See Table IV for analyses.

Table IV provides important details of other related molybdenum derivatives, and their analyses.

Evalutation of Products

Table V, following, provides the results of bench tests of the oil-soluble molybdenum salts of this invention in motor oil formulations. The parameters evaluated were the preventative efforts of the Mo additives on (1) oxidative thickening (Bench IID predicts a passing Seq. IID engine test if viscosity increase does not exceed 200%), (2) bearing corrosion (Bench L-38 result of less than 40 mg. predicts a pass in the CRC-L-38 engine test), (3) wear, and (4) friction reduction.

The additives of the invention were evaluated for use in lubricating oils by various tests known in the lubricating art. Of these, the Bench IIID Test measures the oil thickening tendencies of motor oils under high temperature conditions. The test consists of oxidizing a sample of oil in the presence of air with an iron and copper catalyst at 340° F. After 24, 48 and 72 hours the percent increases in viscosity at 40° C. and milliliters evaporation loss are determined on the oxidized oil. After 24 and 48 hours fresh make-up oil is added to the oxidized oil.

The Bench L-38 Test simulates in a journal bearing rig, the conditions which are produced in the engine test of Federal Method No. 791a, Method 3405.1, and provides a method for studying the copper-lead bearing corrosion characteristics of crankcase oils. The copper strip test is based on ASTM Method D-130 and involves immersing a polished copper strip in a given quantity of neat oils and oils containing the additive under test and heating for a temperature and time characteristic of the material being tested. At the end of this period the copper strip is removed, washed and compared with the ASTM Copper Strip Corrosion Standards.

The third test employed was the Four Ball Wear Test described in U.S. Pat. No. 3,384,588 which measures the amount of wear a lubricating oil permits under engine test conditions with and without additives to be tested. The greater amount of wear, the poorer the ability of the test oil composition to prevent such wear. This wear is measured in terms of the wear scar diameter. This test was run here for 2 hours at 600 rpm/200° F./40 kg load. The friction coefficient was measured at the end of the test when the anti-friction film is fully developed.

The Small Engine Friction Test is a single cylinder engine test which measures the frictional characteristics of an oil. The values given in Table I are based on the torque required to motor an engine containing the oil under test. The results of this test have been found to correlate with field experience using a large fleet of cars under varied on-the-road driving conditions as the percentage change in torque correlates with a percent change in fuel economy.

a. Oxidation, Corrosion and Wear Tests

Blends B through E compare the molybdenum additives substituted for a zinc dialkyldithiophosphate (compare to Blend A). The Mo dialkyldithiophosphate additives in blends B-E were essentially equivalent to the zinc additive (blended at identical phosphorus concentrations) in oxidative thickening and bearing corrosion inhibition, and possible superior in wear. The anti-wear improvement may be due to the enhancement of load carrying properties on substituting Mo for Zn.

b. Friction Tests

Blends F through K were employed to evaluate the subject molybdenum additives in the presence of a conventional zinc dialkyldithiophosphate. The bench test data show that, in addition to providing suitable performance in the previously discussed performance areas, the molybdenum dialkyldithiophosphates (Examples IIa, IV, and VII) were very effective in reducing friction. The friction reductions were much greater than the test variability. The molybdenum salt of the alcoholyzed olefin P$_2$S$_5$ reaction product (Example XV in blend K) provided a lower but probably significant anti-frictional effect also.

Alkyl benzene types of synthetic oils such as tetradecylbenzene, etc., are also included.

It is to be understood that the examples presented herein are intended to be merely illustrative of the invention and not as limiting it in any manner; nor is the invention to be limited by any theory regarding its operability. Consequently, the scope of the invention is to be determined by the appended claims.

TABLE IV

PREPARATION AND ANALYSES OF Mo DERIVATIVES OF OLEFIN:P$_2$S$_5$ PRODUCTS

| Example Number | Olefin:P$_2$S$_5$ Rx Product | Further Rx With | Charge of Mo:P (Molar) | Solvents (ml./G.Atom of Mo) Hydrocarbon | Solvents (ml./G.Atom of Mo) Polar | Product Analyses % Mo | Product Analyses % P | Product Analyses % S |
|---|---|---|---|---|---|---|---|---|
| XII | n-octadecene-1 | — | 1:2 | Heptane–Toluene (1000)–(800) | — | 7.6 | 6.7 | 14.8 |
| XIII | n-octadecene-1 | — | 1:2 | Heptane (333) | Ethyl acetate (1333) | 10:35 | | 13:3 |
| XIV | n-Tetradecene-1 | — | 1:2 | Heptane (1000) | Ethyl acetate (1000) | 9:54 | 8:0 | 20:0 |
| XV | n-Tetradecene-1 | N—C$_{12-14}$ alcohol | 1:2 | Heptane (1810) | Ethyl acetate (790) | 5:32 | 5.5 | 10.4 |
| XVI | n-Tetradecene-1 | 2-propanol | 1:2 | Heptane (1180) | Ethyl acetate (235) | 7.9 | 7.8 | 14.5 |

TABLE V

BENCH TEST PERFORMANCE OF OIL FORMULATIONS CONTAINING MOLYBDENUM ADDITIVES

| Oil Blend | Mo Additive Example No. | Wt. % | % Mo | Zn DTP (2) % ZN | Total % P | B-IIII D % Vis. Incr (2) | B L-38 mg. BWL | 4-Ball Wear, mm | Small Engine Friction Test (3) % Friction Reduction at 280° |
|---|---|---|---|---|---|---|---|---|---|
| A | — | None | — | 0.11 | 0.1 | 46.6 | 34.2 | 0.46 | — |
| B | Ia | 2.0 | 0.18 | None | 0.1 | 31.4 | 0.9 gain | 0.36 | — |
| C | IIa | 2.1 | 0.28 | None | 0.1 | 60.6 | 21.4 gain | 0.36 | — |
| D | IV | 0.4 | 0.06 | None | 0.025 | — | — | 0.36 | — |
| E | XV | 1.78 | 0.095 | None | 0.1 | 60 | 2.2 | 0.38 | — |
| F | IV | 0.4 | 0.06 | 0.127 | 0.14 | 76.1 | 17.7 | 0.37 | — |
| G | VII | 1.0 | 0.05 | 0.09 | 0.1 | 65 | 32.6 | 0.36 | — |
| H | IIa | 0.6 | 0.08 | 0.15 | 0.16 | 86.4 | — | — | 15 |
| I | IV | 0.54 | 0.08 | 0.11 | 0.14 | 81.9 | 17.8 | — | 13 |
| J | VII | 1.14 | 0.055 | 0.11 | 0.17 | 112.7 | — | 0.51 | 16 |
| K | XV | 0.50 | 0.025 | 0.11 | 0.17 | — | 27.5 | — | 5 |
| L | — | None | | 0.11 | 0.13 | — | 26.6 | 0.41 | 0 ± 2 |

(1) The base formulation is a 10W-40 grade oil containing an alkenyl succinimide (0.08% N), an overbased Ca sulfonate (0.23% Ca), an alkylated arylamine (0.25% wt.), an ethoxylated alkylphenol (0.15%), a pour depressant, an ethylene-propylene copolymer VI improver, and an antifoamant. The test oils also contained the indicated amounts of molybdenum additive and a commercial zinc dialkyldithiophosphate.
(2) The increase in kinematic viscosity at 40° C.

Lubricating compositions according to the present invention contain at least one of the products thereof in an amount ranging from about 0.1 to 75.0 percent; preferably between 0.5 and 10.0 percent by weight so as to provide 0.01 to 0.20 weight percent of molybdenum metal.

These compositions can also contain a combination of other well known additives in an amount sufficient to achieve each additive's function.

Lubricating compositions according to this invention comprise a major amount of any of the well-known types of oils of lubricating viscosity as suitable base oils. They include hydrocarbon or mineral lubricating oils of naphthenic, paraffinic and mixed naphthenic and paraffinic types. Such oils may be refined by any of the conventional methods such as solvent refining and acid refining. Synthetic hydrocarbon oils of the alkylene polymer type or those derived from coal and shale may also be employed. Alkylene oxide polymers and their derivatives such as the propylene oxide polymers and their ethers and esters in which the terminal hydroxyl groups have been modified are also suitable. Synthetic oils of the dicarboxylic acid ester type including dibutyl adipate, di-2-ethyl-hexyl sebacate, di-n-hexyl fumaric polymer, dilauryl azelate, and the like may be used.

What is claimed is:

1. In a process for making a lubricating oil additive comprising:

effecting an oxidation reduction reaction at between room temperature and 80° C., between a tri- to hexavalent oxymolybdenum compound and at least one organophosphorus acid or acid precursor consisting of an olefin: P$_2$S$_5$ reaction product or of an alcoholyzed olefin: P$_2$S$_5$ reaction product wherein the olefin moiety contains from 3 to 30 carbon atoms;

the improvement comprising the combination of steps of:

employing said acid or acid precursor in a molar charge ratio with said oxymolybdenum compound of Mo:P of 1:1 to 1:2;

in a mixture of an inert solvent with a polar, oxygen-containing, co-solvent selected from the group consisting of esters, ethers, alcohols, ketones, lactones, amides, lactams and mixtures thereof;

using a ratio of polar cosolvent to solvent ranging from 1:10 to 10:1;

removing the water of reaction formed:

filtering; and, removing said solvent and cosolvent to recover said additive.

2. The process of claim 1, wherein said cosolvent is ethyl acetate, ethylene glycol dimethyl ether, or isopropanol.

3. The process of claim 1, wherein the oxymolybdenum compound is obtained by acidification of an ammonium or alkali metal molybdate.

4. The process of claim 1, wherein said inert solvent is heptane, hexane or cyclohexane.

5. The process of claim 1, wherein said alkyl groups are 2-ethylhexyl.

6. The process of claim 1, wherein said alkyl groups are isopropyl.

7. The process of claim 1, wherein the alkyl groups are a mixture of n-tetradecenyl and n-dodecyl groups.

8. The process of claim 1, wherein said precursor is obtained by reacting an olefin: P$_2$S$_5$ reaction product of the formula:

R''$_2$P$_2$S$_3$ wherein

R'' is an alkenyl group derived from a linear or branched olefin having 4 to 40 carbon atoms;

with an alcohol;

to form said precursor which has the formula:

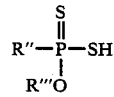

wherein

R' is an alkyl group having 3 to 30 carbon atoms;

prior to reaction with said oxymolybdenum compound.

9. The process of claim 8, whein the R'' group is n-tetradecenyl.

10. The process of claim 8, wherein the R'' group is n-octadecenyl.

11. The process of claim 8, wherein R'' is n-tetradecenyl and R' is derived from a mixture of n-dodecyl and n-tetradecyl alcohols.

12. The process of claim 8, wherein R'' is n-tetradecenyl and R' is isopropyl.

* * * * *